United States Patent [19]

Frump

[11] 4,084,054

[45] Apr. 11, 1978

[54] SUBSTITUTED TRIAZONES

[75] Inventor: John Adams Frump, Terre Haute, Ind.

[73] Assignee: IMC Chemical Group, Inc., Terre Haute, Ind.

[21] Appl. No.: 669,357

[22] Filed: Mar. 22, 1976

[51] Int. Cl.² .......................................... C07D 251/22
[52] U.S. Cl. .................................. 544/220; 424/249
[58] Field of Search .................. 260/248 NS; 544/220

[56] References Cited

U.S. PATENT DOCUMENTS

| | | | |
|---|---|---|---|
| 2,115,550 | 4/1938 | Ellis | 260/248 NS |
| 2,304,624 | 12/1942 | Burke | 260/248 |
| 2,321,989 | 6/1943 | Burke | 260/248 |
| 2,641,554 | 6/1953 | Meunier et al. | 260/248 NS |
| 2,641,584 | 6/1953 | Martone | 260/248 NS |
| 2,901,463 | 8/1959 | Hurwitz | 260/248 X |
| 3,484,439 | 12/1969 | McGonigal | 260/248 |
| 3,501,467 | 3/1970 | Shay et al. | 260/248 |
| 3,505,323 | 4/1970 | Luckenbaugh | 260/248 |
| 3,899,489 | 8/1975 | Horlein et al. | 260/248 |
| 4,007,274 | 2/1977 | Hunsucker | 544/220 |

*Primary Examiner*—John M. Ford
*Attorney, Agent, or Firm*—Robert H. Dewey; Howard E. Post

[57] ABSTRACT

Substituted triazones represented by the formula

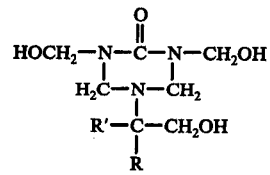

where R and R' are hydrogen, methyl, hydroxymethyl or ethyl and can be the same or different. The compounds have utility as bactericides and fungicides.

3 Claims, No Drawings

SUBSTITUTED TRIAZONES

BACKGROUND OF THE INVENTION

This invention relates to substituted triazones. In a particular aspect, this invention relates to substituted triazones having anti-bacterial and anti-fungal properties.

Although many anti-bacterial and anti-fungal agents are known, many of the previously-used ones have been found to have disadvantages, such as lack of stability, ability of the organism to develop resistance, contribution to environmental pollution, development of toxic reactions by individuals inadvertently exposed to them, etc. Accordingly, there is an ever-present need for new anti-bacterial and anti-fungal agents.

SUMMARY OF THE INVENTION

It is an object of this invention to provide substituted triazones.

It is another object of this invention to provide substituted triazones having anti-bacterial and anti-fungal properties.

Other objects will be apparent to those skilled in the art from the disclosure herein.

It is the discovery of this invention to provide a method of controlling the growth of bacteria and fungi by applying to the environment inhabited by them a compound represented by the formula

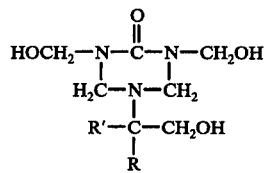

where R and R' are hydrogen, methyl, hydroxymethyl or ethyl and can be the same or different except that R and R' are not both hydrogen.

DETAILED DISCUSSION

The compounds of this invention are prepared by reacting dimethylol urea, which is a known compound, commercially available, with an alkanolamine represented by the formula

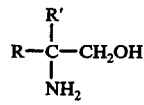

where R and R' have the same meanings defined above, and condensing the product so obtained with formaldehyde to yield a compound represented by formula I, above. The preferred compound is that obtained from 2-amino-2-methyl-1-propanol.

Suitable alkanolamines represented by the above formula include ethanolamine, 2-amino-propanol, 2-amino-2-methyl-1-propanol, 2-amino-1-butanol, 2-amino-2-methyl-1,3-propanediol, 2-amino-2-ethyl-1,3-propanediol, and 2-amino-2-hydroxymethyl-1,3-propanediol. These alkanolamines are all commercially available and the usual commercial grades are suitable for the practice of this invention.

In general, the compounds are prepared by reacting dimethylol urea with the alkanolamine in a mole ratio of about 1:1. The reaction proceeds at room temperature, but should be heated to about 95°–100° C to finish it. The product, which is believed to correspond to the formula

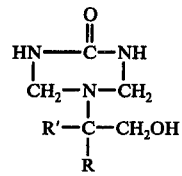

where R and R' have the same meaning hereinbefore defined, is then stripped of volatiles at reduced pressure, e.g. 50° at 20 mm. It is then cooled to room temperature and 2 moles of formaldehyde are added. Condensation proceeds at room temperature, but heat, e.g. up to about 100° C or more, can be applied to accelerate the reaction if preferred. The product so obtained is usually in aqueous solution (if aqueous formaldehyde is used) and the solution is suitable for use in the practice of this invention.

The formaldehyde used in the practice of this invention is preferably the ordinary 37% aqueous formaldehyde of commerce. However, the 44% grade is equally useful as are the solutions of formaldehyde in the lower alkanols. Formaldehyde from a formaldehyde source can also be used if desired.

The compounds of this invention can be used in any manner known in the art, of which there are many. Generally, they will be used in aqueous systems as preservatives, e.g. in cutting oils, protein adhesives, latex paints and the like. When preferred, however, they can be applied in the form of dusts, sprays and the like.

The invention will be better understood with reference to the following examples. It is understood, however, that the examples are intended only to illustrate the invention, and it is not intended that the invention be limited thereby.

EXAMPLE 1

Dimethylol urea was prepared by delivering to a reaction vessel 60 g of urea (1 mole) and 162 g of 37% aqueous formaldehyde (2 moles). The reaction vessel was fitted with an agitator and thermometer. The pH was adjusted to 7.0 with sodium hydroxide. The mixture was stirred well, then allowed to stand at room temperature for about 3 hours. Then 89 g of 2-amino-2-methyl-1-propanol, 1 mole, was added while maintaining a temperature of 5°–15° C. The mixture was then allowed to warm slowly to room temperature where it was maintained about an hour. It was then heated at 95°–100° C for about 2 hours. Volatiles were stripped by vacuum distillation until the pot temperature reached 50° at 20 mm.

The reaction mixture was cooled to room temperature and 162 g of 37% formaldehyde (2 moles) was added. It was agitated for about 3 hours at room temperature and allowed to stand overnight. The resulting product contained about 64% of tetrahydro-1,3-bis(hydroxymethyl)-5-(2-hydroxy-1,1-dimethylethyl)-1,3,5-triazin-2(1H)-one in water.

The compound was tested for anti-bacterial and anti-fungal activity by determining the minimum inhibitory concentration range for 9 bacteria and 8 fungi. In the range given below, the lower figure is the highest concentration at which growth occurred and the higher figure is the lowest concentration tested at which no growth of organism occurred. The results are as follows:

| Bacteria | Minimum Inhibitory Concentration, ppm |
|---|---|
| *Bacillus subtilis* | 500–1000 |
| *Staphylococcum aureus* | 500–1000 |
| *Streptococcus faecalis* | 1000–2000 |
| *Sarcina lutea* | 1000–2000 |
| *Escherichia coli* | 1000–2000 |
| *Aerobacter aerogenes* | 1000–2000 |
| *Pseudomonas aeruginosa* | 500–1000 |
| *Salmonella typhi* | 250–500 |
| *Desulfovibrio aestuarii* | 500–1000 |

| Fungi | Minimum Inhibitory Concentration, ppm |
|---|---|
| *Cladosporium herbarum* | 1000–2000 |
| *Cephalosporium species* | 32.25–64.5 |
| *Trichophyton mentagrophytes* | 125–150 |
| *Aspergillus niger* | 500–1000 |
| *Aureobasidium pullulans* | 500–1000 |
| *Fusarium moniliforme* | >2000 |
| *Saccharomyces cerevisiae* | 64.5–125 |
| *Candida albicans* | 125–250 |

It is determined that the product is useful as a preservative in latex paints and cutting oils.

EXAMPLE 2

The experiment of Example 1 is repeated in all essential details except that ethanolamine is substituted for 2-amino-2-methyl-1-propanol on an equimolar basis. The product obtained is tetrahydro-5-(2-hydroxyethyl)-1,3-bis(hydroxymethyl)-1,3,5-triazin-2(1H)-one. It is effective as a preservative at concentrations of 500 ppm to 3000 ppm or more.

EXAMPLE 3

The experiment of Example 1 is repeated in all essential details except that 2-amino-1-butanol is substituted for 2-amino-2-methyl-1-propanol on an equimolar basis. The product obtained is tetrahydro-1,3-bis(hydroxymethyl)-5-[1-hydroxymethyl)propyl]-1,3,5-triazin-2(1H)-one. It is effective as a preservative at concentrations of 500 ppm to 3000 ppm or more.

EXAMPLE 4

The experiment of Example 1 is repeated in all essential details except that 2-amino-2-methyl-1,3-propanediol is substituted for 2-amino-2-methyl-1-propanol on an equimolar basis. The product obtained is tetrahydro-1,3-bis(hydroxymethyl)-5-[1,1-bis(hydroxymethyl)ethyl]-1,3,5-triazin-2(1H)-one. It is effective as a preservative at concentrations of 500 ppm to 3000 ppm or more.

EXAMPLE 5

The experiment of Example 1 is repeated in all essential details except that 2-amino-2-ethyl-1,3-propanediol is substituted for 2-amino-2-methyl-1-propanol on an equimolar basis. The product obtained is tetrahydro-1,3-bis(hydroxymethyl)-5-[1,1-bis(hydroxymethyl)propyl]-1,3,5-triazin-2(1H)-one. It is effective as a preservative at concentrations of 500 ppm to 3000 ppm or more.

EXAMPLE 6

The experiment of Example 1 is repeated in all essential details except that 2-amino-2-hydroxymethyl-1,3-propanediol is substituted for 2-amino-2-methyl-1-propanol on an equimolar basis. The product obtained is tetrahydro-1,3-bis(hydroxymethyl)-5-[2-hydroxy-1,1-bis(hydroxymethyl)ethyl]-1,3,5-triazin-2(1H)-one.

EXAMPLE 7

The experiment of Example 1 is repeated in all essential details except that 2-amino-1-propanol is substituted for 2-amino-2-methyl-1-propanol on an equimolar basis. The product obtained is tetrahydro-1,3-bis(hydroxymethyl)-5-(2-hydroxy-1-methylethyl)-1,3,5-triazin-2(1H)-one. It is effective as a preservative at concentrations of 500 ppm to 3000 ppm or more.

I claim:

1. A compound represented by the formula

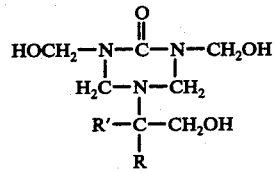

where R is hydroxymethyl and R' is methyl or ethyl.

2. A compound represented by the formula

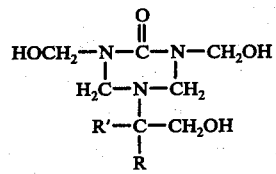

where R and R' are methyl.

3. A compound represented by the formula

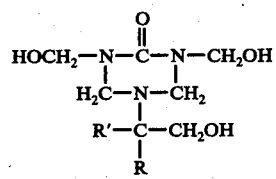

where R and R' are hydroxymethyl.

* * * * *